United States Patent
Beller et al.

[11] Patent Number: 5,886,240
[45] Date of Patent: Mar. 23, 1999

[54] PROCESS FOR PREPARING AROMATIC ACETYLENES USING PALLADACYCLES AS CATALYSTS

[75] Inventors: Matthias Beller, Idestein; Claus Peter Reisinger, Graiching; Wolfgang Anton Herrmann, Freising, all of Germany

[73] Assignee: Hoechst Aktiengesellschaft, Germany

[21] Appl. No.: 635,409

[22] Filed: Apr. 26, 1996

[30] Foreign Application Priority Data

Apr. 27, 1995 [DE] Germany .................. 195 15 444.4

[51] Int. Cl.$^6$ .................................... C07C 37/02
[52] U.S. Cl. ................ 568/797; 568/780; 568/939; 568/795; 556/136
[58] Field of Search ................ 568/797, 780, 568/939, 795; 556/136

[56] References Cited

U.S. PATENT DOCUMENTS 3,632,824  1/1972  Fitton .
4,128,588  12/1978  Sabourin .

FOREIGN PATENT DOCUMENTS 0 688 757  12/1995  European Pat. Off. .
0 688 779  12/1995  European Pat. Off. .

OTHER PUBLICATIONS

J. Org. Chem, Mitsudo, vol. 49, pp. 1640–1646, 1984.
March "Advanced Organic Chemistry" 1968 p. 552.
CA 100:209245 –Abst. of J. Organ Chem "Palladiumcatalyzed syntheses of aryl polyenes" 1984.
J. Mol. Catal. A: Chem; vol. 108; pp. 51–56; Herrmann W A et al: "Coordination chemistry and mechanisms of metal–catalyzed C–C coupling reactions. Part 8. Facile catalytic coupling of aryl bromides with terminal alkynes by phospha–palladacycles".
Bulletin of The Academy of Sciences of the USSR Division of Chemical Science., Bd. 37, Nr. 3, 1988, New York, US, pp. 507–509; N.A. Bumagin et al: "Reactions of terminal acetylenes with aryl iodides catalyzed by palladium complexes under interfacial conditions".
Dieck, H. A., et al, *J. of Organometallic Chem.* 93: 259–263 (1975).

Primary Examiner—Alan L. Rotman
Assistant Examiner—Jean F. Vollano
Attorney, Agent, or Firm—Connolly and Hutz

[57] ABSTRACT

The invention relates to a process for preparing aromatic acetylenes of the formula (I): $Ar-C\equiv C-R^{8a}$, where Ar is:

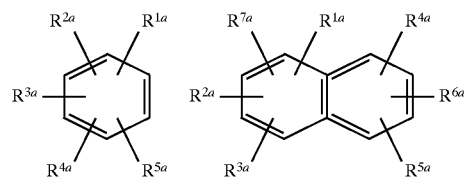

by reacting haloaromatics or aryl sulfonates of the formula (II): $Ar-X$, with monosubstituted acetylenes of the formula (III): $Ar-C\equiv C-R^{8a}$, where Ar is defined above and X is bromine, chlorine or $OSO_2R$, in the presence of a palladium compound catalyst of the formula (IV):

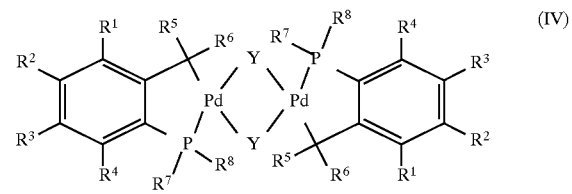

where $R^1$, $R^2$, $R^3$, $R^4$, $R^5$, $R^6$ are, independently of one another, hydrogen ($C_1$–$C_4$)-alkyl, ($C_1$–$C_4$)-alkoxy, fluorine, $NH_2$, NH-alkyl-($C_1$–$C_4$), N(alkyl)$_2$-($C_1$–$C_4$), $CO_2$-alkyl-($C_1$–$C_4$), OCO-alkyl-($C_1$–$C_4$), or phenyl, or $R^1$ and $R^2$, $R^2$ and $R^3$, $R^3$ and $R^4$, $R^5$ and $R^6$, together form an aliphatic or aromatic ring, and $R^7$, $R^8$ are ($C_1$–$C_8$)-alkyl, ($C_3$–$C_{12}$)-cycloalkyl, substituted or unsubstituted aryl, and Y is an anion of an inorganic or organic acid.

17 Claims, No Drawings

PROCESS FOR PREPARING AROMATIC ACETYLENES USING PALLADACYCLES AS CATALYSTS

The present invention relates to a new process for preparing aromatic acetylenes using novel catalysts, so-called palladacycles.

Aromatic acetylenes, in particular diphenylacetylene derivatives, have industrial importance as structural units of liquid crystals and precursors for active compounds.

A frequently used method of synthesizing aromatic acetylenes on the laboratory scale is palladium-catalyzed coupling in which iodoaromatics, bromoaromatics and, in exceptional cases, chloroaromatics are reacted with mono-substituted acetylenes in the presence of palladium catalysts and generally catalytic amounts of copper(I) iodide as cocatalyst. Examples describing this methodology can be found in H. A. Dieck, R. F. Heck, J. Organomet. Chem., 93 (1975) 259; R. F. Heck, Palladium Reagents in Synthesis, Academic Press, London 1985.

Despite the numerous publications on the subject of synthesizing aromatic acetylenes in the presence of palladium catalysts, no examples of industrial use of the methodology have been known hitherto. This can be attributed to the fact that the catalyst systems described frequently require addition of large amounts of palladium catalyst and copper(I) iodide as cocatalyst, in both cases from 1 to 10 mol %, to achieve industrially utilizable conversions. Owing to the complexity of the reaction mixtures, simple catalyst recycling is not possible, so that the catalyst costs generally make industrial implementation difficult.

For the above reasons, it is of great industrial interest to find better, industrially utilizable catalyst systems for the synthesis of aromatic acetylenes generally and in particular for the use of economically favorable bromo-aromatics. There is therefore a great need for a process which avoids the disadvantages described and makes it possible to obtain aromatic acetylenes in a technically simple manner.

This object is achieved by a process for preparing aromatic acetylenes of the formula (I)

$$Ar-C{\equiv}C-R^{8a} \quad (I)$$

where

Ar is

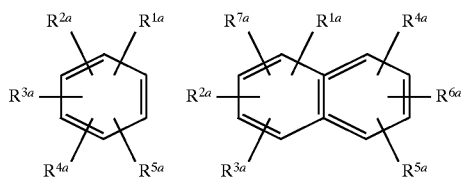

and $R^{1a}$ to $R^{7a}$ are, independently of one another, hydrogen, $C_1$–$C_8$-alkyl, alkoxy-($C_1$–$C_8$), acyloxy-($C_1$–$C_8$), O-phenyl, phenyl, fluorine, chlorine, bromine, OH, $NO_2$, CN, COOH, CHO, $SO_3H$, $SO_2R$, SOR, wherein R is $C_1$–$C_8$-alkyl or phenyl, $NH_2$, NH-alkyl-($C_1$–$C_{12}$), N-alkyl$_2$-($C_1$–$C_{12}$), C-Hal$_3$, NHCO-alkyl-($C_1$–$C_8$), CO-alkyl-($C_1$–$C_8$), COO-alkyl-($C_1$–$C_{12}$), CONH$_2$, CO-alkyl-($C_1$–$C_{12}$), NHCOH, NCOO-alkyl-($C_1$–$C_8$), CO-phenyl, COO-phenyl, CHCHCO$_2$-alkyl-($C_1$–$C_{12}$), CHCHCO$_2$H, PO-phenyl$_2$, PO-alkyl$_2$-($C_1$–$C_8$), 5-membered ring heteroaryl or 6-membered ring heteroaryl and $R^{8a}$ is H, ($C_1$–$C_{12}$)-alkyl, Si(CH$_3$)$_3$, CH$_2$OH, C(CH$_3$)$_2$OH or Ar, by reacting haloaromatics or aryl sulfonates of the formula (II)

$$Ar-X \quad (II)$$

with monosubstituted acetylenes of the formula (III)

$$H-C{\equiv}C-R^{8a} \quad (III)$$

where Ar and $R^{8a}$ are as defined above and X is bromine or chlorine or $OSO_2R$, wherein R is $C_1$–$C_8$alkyl or phenyl, and wherein a palladium compound of the formula (IV)

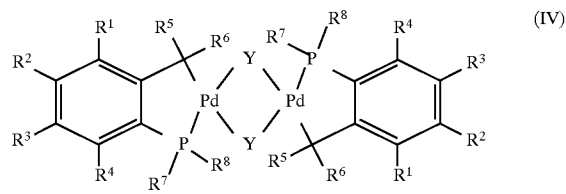

where $R^1$, $R^2$, $R^3$, $R^4$, $R^5$, $R^6$ are, independently of one another, hydrogen, ($C_1$–$C_4$)-alkyl, ($C_1$–$C_4$)-alkoxy, fluorine, $NH_2$, NH-alkyl-($C_1$–$C_4$), N(alkyl)$_2$-($C_1$–$C_4$) $CO_2$-alkyl-($C_1$–$C_4$), OCO-alkyl-($C_1$–$C_4$) or phenyl, or $R^1$ and $R^2$, $R^2$ and $R^3$, $R^3$ and $R^4$, $R^5$ and $R^6$ together form an aliphatic or aromatic ring, and $R^7$, $R^8$ are ($C_1$–$C_8$)-alkyl, ($C_3$–$C_{12}$)-cycloalkyl, substituted or unsubstituted aryl and Y is an anion of an inorganic or organic acid, is used as catalyst.

The process is important for preparing compounds of the formula (I) in which $R^{1a}$ to $R^{7a}$ in formula (I) are hydrogen, ($C_1$–$C_4$)-alkyl, alkoxy-($C_1$–$C_4$), acyloxy-($C_1$–$C_4$), O-phenyl, O-phenyl, phenyl, fluorine, chlorine, OH, $NO_2$, CN, COOH, CHO, $NH_2$, NH-alkyl-($C_1$–$C_6$), N-alkyl$_2$-($C_1$–$C_6$), NHCO-alkyl-($C_1$–$C_4$), CO-alkyl-($C_1$–$C_4$), COO-alkyl-($C_1$–$C_6$), CONH$_2$, CO-alkyl-($C_1$–$C_6$), NHCOH, NCOO-alkyl-($C_1$–$C_4$), CHCHCO$_2$-alkyl-($C_1$–$C_6$), CHCHCO$_2$H, 5-membered ring heteroaryl or 6-membered ring heteroaryl.

The process is of interest for preparing compounds of the formula (I) in which 3, in particular 4, of the substituents $R^{1a}$ to $R^{7a}$ are hydrogen and the remaining substituents are as defined above.

The process is of great importance, for example, for preparing the following compounds: 1-(4-nitrophenyl)-2-phenylethyne, 1-(4-acetylphenyl)-2-phenylethyne, 2-(6-methoxynaphthyl)-1-trimethylsilylethyne, 3-(6-methoxynaphthyl)-1-methylpropargyl alcohol, (4-isobutyl-phenyl)- 1-ethyne, 6-methoxynaphthyl-2-ethyne, 4-hydroxyphenyl-1-ethyne, 4-(2-hydroxyethoxy)phenyl-1-ethyne, 1-(4-chlorophenyl)-2-phenylethyne, 1-(4-n-butyl-phenyl)-2-phenylethyne, 1-(4-methoxyphenyl)-2-phenyl-ethyne, 3-(4-acetylphenyl)-1-trimethylsiloxyprop-2-yne, 3-(4-acetylphenyl)-1-tetrahydropyranylprop-2-yne, 3-(4-chlorophenyl)-1-trimethoxysiloxyprop-2-yne, 3-(4-chloro-phenyl)-1-tetrahydropyranylprop-2-yne, 1-(2-pyridyl)-2-phenylethyne and 4-(6-methoxynaphthyl) -1-methylbut-2-yn-1-ol.

Compounds of the formula (IV) which have been found to be useful in many cases are those in which $R^1$ to $R^6$ are hydrogen, alkyl-($C_1$–$C_4$), phenyl, cycloalkyl-($C_5$–$C_8$), $R^7$ and $R^8$ are phenyl, tolyl, xylyl, mesityl, alkyl-($C_1$–$C_8$) and cycloalkyl-($C_5$–$C_8$) and Y is acetate, propionate, benzoate, chloride, bromide, iodide, fluoride, sulfate, hydrogensulfate, nitrate, phosphate, tetrafluoroborate, tosylate, mesylate, acetylacetonate, hexafluoroacetyl-acetonate, or pyrazolyl.

Well suited compounds of the formula (IV) are, for example, those in which $R^1$ to $R^6$ are H, alkyl, phenyl and $R^7$, $R^8$ are alkyl, phenyl, tolyl, mesityl and xylyl.

Very good results are given by the compounds:

trans-di-$\mu$-acetato-bis[o-(di-o-tolylphosphino)benzyl]dipalladium(II)

trans-di-$\mu$-chloro-bis[o-(di-o-tolylphosphino)benzyl]dipalladium(II)

trans-di-$\mu$-bromo-bis[o-(di-o-tolylphosphino)benzyl]dipalladium(II)

trans-di-$\mu$-iodo-bis[o-(di-o-tolylphosphino)benzyl]dipalladium(II)

trans-di-$\mu$-acetato-bis[o-(dimesitylphosphino)-3,5-dimethylbenzyl]dipalladium(II)

trans-di-$\mu$-chloro-bis[o-(dimesitylphosphino)-3,5-dimethylbenzyl]dipalladium(II)

trans-di-$\mu$-bromo-bis[o-(dimesitylphosphino)-3,5-dimethylbenzyl]dipalladium(II)

trans-di-$\mu$-iodo-bis[o-(dimesitylphosphino)-3,5-dimethylbenzyl]dipalladium(II)

Solvents used are generally inert organic solvents. Preference is given to using dipolar aprotic and polar solvents, in particular alkylated amines. The particularly preferred solvent is triethylamine.

Since hydrogen halide is eliminated during the reaction, it is advantageous to neutralize this by addition of a base. Suitable bases for this purpose are primary, secondary or tertiary amines such as alkylamines, dialkylamines, trialkylamines, which can be alicyclic or open-chain.

Apart from these, it is possible to use alkali metal or alkaline earth metal salts of organic compounds having a $PK_a > 7$.

The palladium catalysts used are generally synthesized and isolated prior to the actual reaction, but in some cases they can also be produced in situ.

The process is generally carried out at temperatures of from 20° to 150° C. Temperatures of from 50° to 120° C., in particular from 60° to 100° C., have been found to be useful.

The synthesis of the palladium catalysts used is carried out by a method similar to that described in the German Patent Application No. P 44 21 753.6.

The palladacycles which are used or which form generally have dimeric character. However, in the case of certain compounds, monomeric or polymeric structures can also be present.

Catalyst systems used in the context of the reaction of aryl halides with monosubstituted acetylenes are generally palladium compounds and, in general, copper(I) iodide as cocatalyst. Although both palladium(II) and palladium(0) complexes are used in acetylene couplings, it is generally accepted that only palladium(0) compounds are the actual catalysts of the reaction. Compounds formulated here are frequently coordinatively unsaturated 14 electron palladium (0) species which are generally stabilized using weak donor ligands such as phosphines.

In view of this background, the advantages of the catalysts used in the process of the invention are particularly surprising.

The palladacycles used as new catalyst systems have very high activity and, unexpectedly, high stability associated therewith. The catalyst systems described are the most active catalysts up to now for the reaction of the invention. Thus, turnover values in the order of 8000 can be realized.

Owing to the catalyst activities and stability it is possible to use extremely small amounts of catalyst, so that the catalyst costs in comparison with conventional acetylene couplings are not cost-limiting for the corresponding process and the cocatalyst copper(I) iodide can be completely omitted.

In addition, the use of minimal amounts of palladium catalyst and the omission of cocatalyst gives ecological advantages, since both waste products and relatively complicated catalyst recycling can be avoided.

The examples below serve to illustrate the process of the invention, without restricting it thereto.

EXAMPLE 1

2.02 g (10 mmol) of 4-bromonitrobenzene and 1.2 g (12 mmol) of phenylacetylene are heated with 10 g (0.1 mol %) of trans-di-$\mu$-acetato-bis[o-(di-o-tolylphosphino)benzyl]dipalladium(II) in 30 ml of triethylamine for 4 hours at 90° C. The reaction solution is filtered hot to remove the quantitatively precipitated triethylammonium bromide and the product is separated off by means of fractional crystallization.

Yield: 95% of 1-(4-nitrophenyl)-2-phenylethyne.

EXAMPLE 2

2.0 g (10 mmol) or 4-bromoacetophenone and 1.2 g (12 mmol) of phenylacetylene are heated with 10 mg (0.1 mol %) of trans-di-$\mu$-acetato-bis[o-(di-o-tolylphosphino)benzyl]-palladium(II) in 30 ml of triethylamine for 4 hours at 90° C. The reaction solution is filtered hot to remove the quantitatively precipitated triethylammonium bromide and the product is separated off by means of fractional crystallization.

Yield: 96% of 1-(4-acetylphenyl)-2-phenylethyne.

EXAMPLES 3 to 13

2.02 g (10 mmol) of 4-bromonitrobenzene and 1.2 g (12 mmol) of phenylacetylene are heated with 10 mg (0.1 mol %) of catalyst 1 in 30 ml of triethylamine at 90° C. After 4 hours under reflux, the precipitated triethylammonium bromide is filtered off hot, immediately after which the product crystallizes in the filtrate. This gives 1.73 g of 97%-pure 1-(4-nitrophenyl)-2-phenylethyne (corresponds to 80% of theory).

$^1$H-NMR (300 MHz, 20° C., CDCl$_3$); $\delta$=8.2 (2H, m, H$_{Ar, nitro}$), 7.66 (2H, m, H$_{Ar, nitro}$), 7.56 (2H, m, H$_{Ar}$), 7.39 (2H, m, H$_{Ar}$); $^{13}$C{1H}-NMR (75.4 MHz, 20° C., CDCl$_3$): $\delta$=147.0 (s, C—NO$_2$), 132.6 (s, C$_{Ar}$), 132.3 (s, C$_{Ar}$), 131.9 (s, C$_{Ar}$), 130.3 (s, C$_{Ar}$), 129.3 (S, C$_{Ar}$), 128.6 (s, C$_{Ar}$), 125.0 (s, C$_{Ar}$), 123.7 (s, C$_{Ar}$), 94.8 (s, C$_{acetylene}$).

The same method is used to prepare (yield in [%]):

1-(4-acetylphenyl)-2-phenylethyne (99)
1-(4-nitrophenyl)-2-phenylethyne (99)
1-(4-chlorophenyl)-2-phenylethyne (90)
1-(4-n-butylphenyl)-2-phenylethyne (80)
1-(4-methoxyphenyl)-2-phenylethyne (80)
3-(4-acetylphenyl)-1-trimethylsiloxyprop-2-yne (38)
3-(4-acetylphenyl)-1-tetrahydropyranylprop-2-yne (30)
3-(4-chlorophenyl)-1-trimethylsiloxyprop-2-yne
3-(4-chlorophenyl)-1-tetrahydropyranylprop-2-yne (40)
1-(2-pyridyl)-2-phenylethyne (30)
4-(6-methoxynaphthyl)-1-methyl-but-2-yn-1-ol (68)

EXAMPLE 14 catalyst prepared in situ 2.0 g (10 mmol) of 4-bromoacetophenone and 1.2 g (12 mmol) of phenylacetylene are heated with 10 g (0.1 mol %) of palladium acetate and xx mg (0.1 mol %) of tri-o-tolylphosphine in 30 ml of triethylamine for 4 hours at 90° C. The reaction solution is filtered hot to remove the quantitatively precipitated triethylammonium bromide and the product is separated off by means of fractional crystallization.

Yield: 93% of 1-(4-acetylphenyl)-2-phenylethyne.

We claim:

1. A process for preparing aromatic acetylenes of the formula (I): Ar—C≡C—R$^{8a}$
where
Ar is

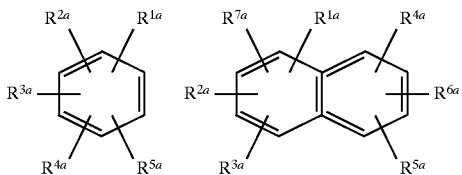

and

R$^{1a}$ to R$^{7a}$ are, independently of one another, hydrogen, C$_1$–C$_8$-alkyl, or phenyl with at least one of the R$^{1a}$ to R$^{7a}$ groups being OH or NO$_2$, and R$^{8a}$ is H, C$_1$–C$_{12}$-alkyl, or Ar, or R$^{1a}$ to R$^{7a}$ are, independently of one another, hydrogen, C$_1$–C$_8$-alkyl, or phenyl, and R$^{8a}$ is H, CH$_2$OH or C(CH$_3$)$_2$OH, by reacting haloaromatics or aryl sulfonates of the formula (II): Ar—X, with monosubstituted acetylenes of the formula (III): H—C≡C—R$^{8a}$, where Ar and R$^{8a}$ are as defined above and X is bromine, chlorine or OSO$_2$R, and where R is C$_1$–C$_8$-alkyl or phenyl, in a presence of a catalyst comprising a palladium compound of the formula (IV):

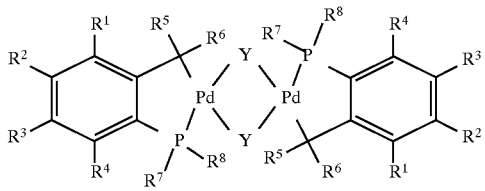

wherein

R$^1$, R$^2$, R$^3$, R$^4$, R$^5$, R$^6$ are, independently of one another, hydrogen (C$_1$–C$_4$)-alkyl, (C$_1$–C$_4$)-alkoxy, fluorine, NH$_2$, NH-alkyl-(C$_1$–C$_4$), N(alkyl)$_2$-(C$_1$–C$_4$), CO$_2$-alkyl-(C$_1$–C$_4$), OCO-alkyl-(C$_1$–C$_4$) or phenyl, or R$^1$ and R$^2$, R$^2$ and R$^3$, R$^3$ and R$^4$, R$^5$ and R$^6$, together form an aliphatic or aromatic ring, and R$^7$, R$^8$ are (C$_1$–C$_8$)-alkyl, (C$_3$–C$_{12}$)-cycloalkyl, substituted or unsubstituted aryl, and Y is an anion of an inorganic or organic acid and in the absence of copper(I) iodine.

2. The process as claimed in claim 1, wherein, in formula (IV), R$^1$ to R$^6$ are, independently of one another, hydrogen, alkyl-(C$_1$–C$_4$), phenyl, cycloalkyl-(C$_5$–C$_8$), R$^7$ and R$^8$ are phenyl, tolyl, xylyl, mesityl, alkyl-(C$_1$–C$_8$) and cycloalkyl-(C$_5$–C$_8$) and Y is acetate, propionate, benzoate, chloride, bromide, iodide, fluoride, sulfate, hydrogensulfate, nitrate, phosphate, tetrafluoroborate, tosylate, mesylate, acetylacetonate, hexafluoroacetylacetonate, or pyrazolyl.

3. The process as claimed in claim 1, wherein, in formula (IV), R$^1$ to R$^6$ are H, alkyl, phenyl, R$^7$, R$^8$ are phenyl, tolyl, xylyl, mesityl and alkyl.

4. The process as claimed in claim 1, wherein the compounds trans-di-μ-acetato-bis[o-(di-o-tolylphosphino)benzyl] dipalladium(II)

trans-di-μ-chloro-bis[o-(di-o-tolylphosphino)benzyl] dipalladium(II)

trans-di-μ-bromo-bis[o-(di-o-tolylphosphino)benzyl] dipalladium(II)

trans-di-μ-iodo-bis[o-(di-o-tolylphosphino)benzyl] dipalladium(II)

trans-di-μ-acetato-bis[o-(dimesitylphosphino)-3,5-dimethylbenzyl]dipalladium(II)

trans-di-μ-chloro-bis[o-(dimesitylphosphino)-3,5-dimethylbenzyl]dipalladium(II)

trans-di-μ-bromo-bis[o-(dimesitylphosphino)-3,5-dimethylbenzyl]dipalladium(II)

trans-di-μ-iodo-bis[o-(dimesitylphosphino)-3,5-dimethylbenzyl]dipalladium(II) are used as catalyst.

5. The process as claimed in claim 1, wherein the catalyst is prepared in situ.

6. The process as claimed in claim 1, where 3 or 4 of the substituents R$^{1a}$ to R$^{7a}$ are hydrogen.

7. The process as claimed in claim 1,
wherein formula (I) represents 1-(4-nitrophenyl)-2-phenylethyne, (4-isobutylphenyl)-1-ethyne, 4-hydroxyphenyl-1-ethyne.

8. The process as claimed in claim 1,
wherein dipolar aprotic and polar solvents are used.

9. The process as claimed in claim 1,
wherein the acid HX formed during the reaction is neutralized by addition of base.

10. The process as claimed in claim 9, wherein alkylamines are used as base.

11. The process as claimed in claim 1,
wherein the reaction is carried out at temperatures of from 20° to 150° C.

12. The process as claimed in claim 9 wherein the solvent is a trialkylamine.

13. The process as claimed in claim 12 wherein the solvent is triethylamine.

14. The process as claimed in claim 10 wherein the base is an amine.

15. The process as claimed in claim 11 wherein the base is triethylamine.

16. The process as claimed in claim 11 wherein the reaction is carried out at temperatures of from 20°–150° C.

17. The process as claimed in claim 16 wherein the reaction is carried out at temperatures of from 60° to 110° C.

* * * * *